US00PP21720P3

(12) United States Plant Patent
Patel

(10) Patent No.: US PP21,720 P3
(45) Date of Patent: Feb. 22, 2011

(54) BLUEBERRY VARIETY NAMED 'SKY BLUE'

(50) Latin Name: *Vaccinium virgatum*
Varietal Denomination: Sky Blue

(75) Inventor: Narandra Patel, Hamilton (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 0 days.

(21) Appl. No.: 12/590,309

(22) Filed: Nov. 5, 2009

(65) Prior Publication Data

US 2010/0115678 P1 May 6, 2010

Related U.S. Application Data

(60) Provisional application No. 61/198,468, filed on Nov. 6, 2008.

(51) Int. Cl.
*A01H 5/00* (2006.01)

(52) U.S. Cl. ..... Plt./157

(58) Field of Classification Search ..... Plt./157
See application file for complete search history.

*Primary Examiner*—Annette H Para
(74) *Attorney, Agent, or Firm*—Greenlee Sullivan PC

(57) ABSTRACT

A new and distinct Rabbiteye blueberry variety is described. The variety results from selection among a population of seedlings derived from crossing the blueberry varieties known as 'Centurion' (not patented) and 'Rahi' (not patented). The fruit of this new variety is large and firm, with an attractive appearance characterized by good bloom; fruit has an outstanding quality with good balance between sugar and acidity. Plant is upright with medium to good vigor and medium yield. The new variety has been named 'Sky Blue'.

7 Drawing Sheets

Genus and species of plant named: *Vaccinium virgatum.*
Variety denomination: Sky Blue.

BACKGROUND OF THE INVENTION

This new rabbiteye blueberry variety was selected from a population of seedlings derived from crossing the blueberry varieties 'Centurion' (not patented) and 'Rahi' (not patented). The new variety was selected in February 2000 from among plants located at Ruakura, Hamilton, New Zealand, and was assigned the breeder code, F110. The new variety has since been named 'Sky Blue'.

SUMMARY OF THE INVENTION

The fruit of this new variety is large and firm, with an attractive appearance characterised by good bloom; fruit has an outstanding quality with good balance between sugar and acidity. Plant is upright with medium to good vigour and medium yield. The new variety was originally referred to as 'F110' but has since been named 'Sky Blue'.

The new variety is characterised as follows:

Maturity period: Mid season, about the same window of 'Rahi' and 3 to 4 weeks earlier than 'Centra Blue' at the Ruakura, Hamilton, New Zealand.

Plant form and vigour: The plant is upright in habit with medium to good vigour.

Yield: Medium.

Berry size: Large, bigger than 'Centurion' and 'Rahi'.

Color: Medium blue.

Fruit bloom: Strong; attractive.

Pedicel scar: Small.

Plant health: The plant has shown symptoms of the early stage of rust infection (*Pucciniastrum vaccinii*) with no subsequent sporulation and no defoliation.

BRIEF DESCRIPTION OF THE PHOTOGRAPHS

The accompanying photographs show typical specimens of the plant, foliage and fruit of the new variety as depicted in colors as nearly true as is reasonably possible to make the same in a color illustration of this character.

DETAILED DESCRIPTION

Figure 1A:
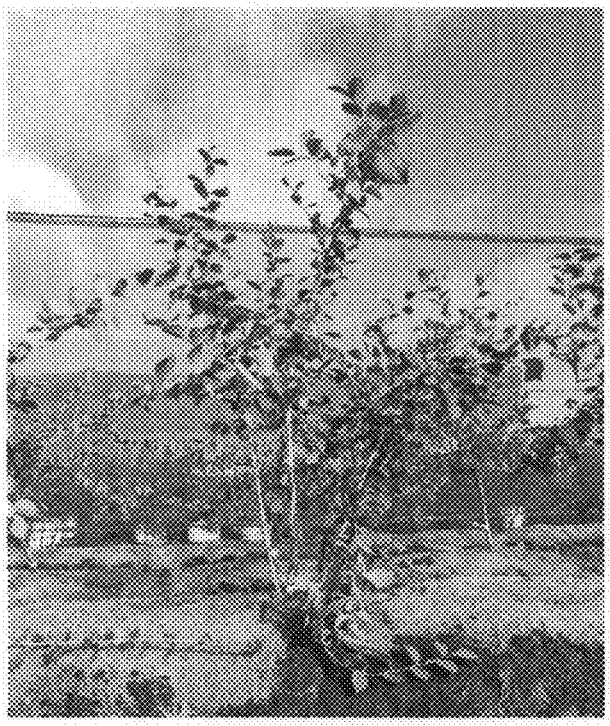
FIG. 1A was taken in April 2008, and FIG. 1B was taken in September 2009.
Figure 1B:
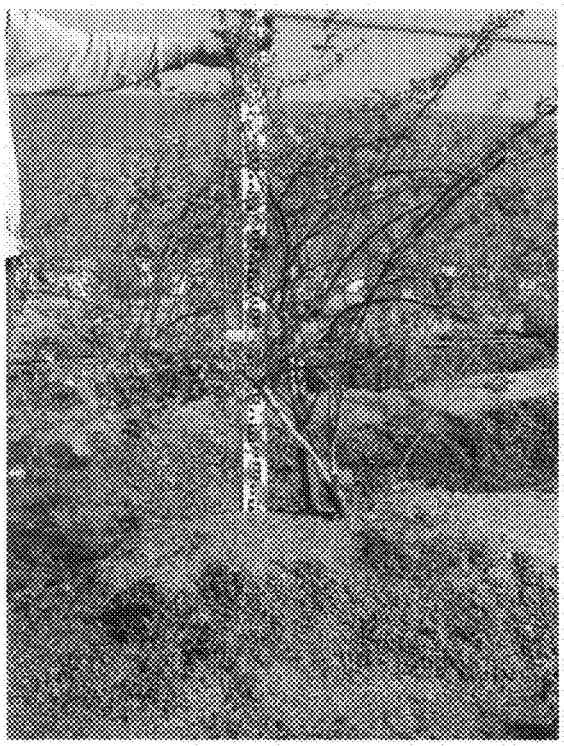
FIG. 1 shows a young plant of 'Sky Blue' planted in the field.
Figure 2:
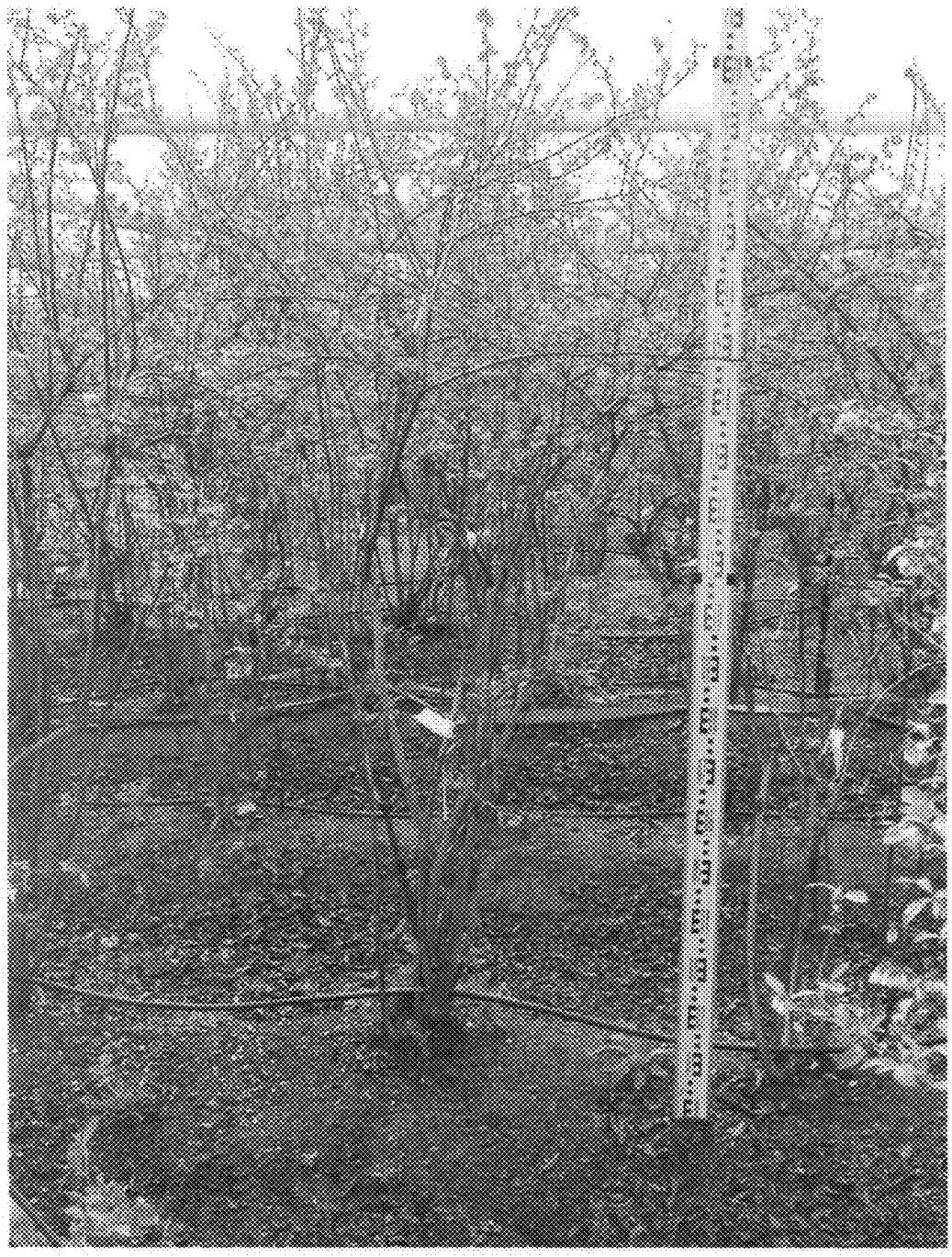
FIG. 2 shows the adult plant of 'Sky Blue' planted in the field (September 2009).
Figure 3A:
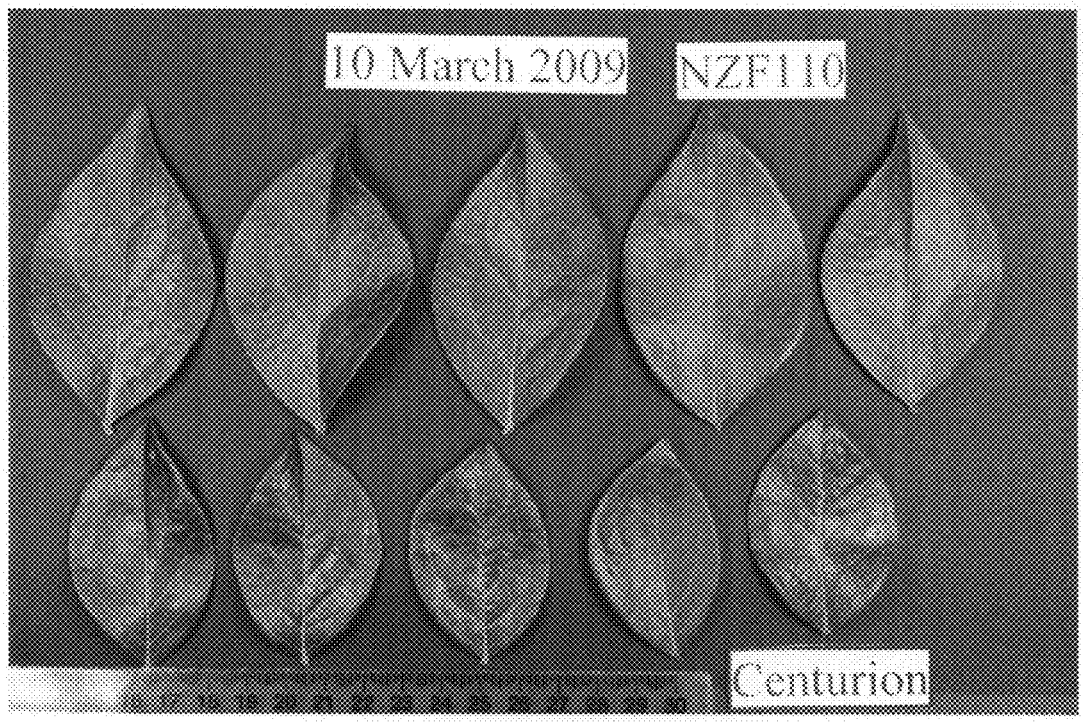
FIG. 3 shows the typical leaves of adult plant of 'Sky Blue' (labeled in FIGS. 3A and 3B as 'NZ F110') collected in New Zealand in March 2009 and compared to the leaves of the parental plants 'Centurion' (FIG. 3A) and 'Rahi' (FIG. 3B).
Figure 3B:
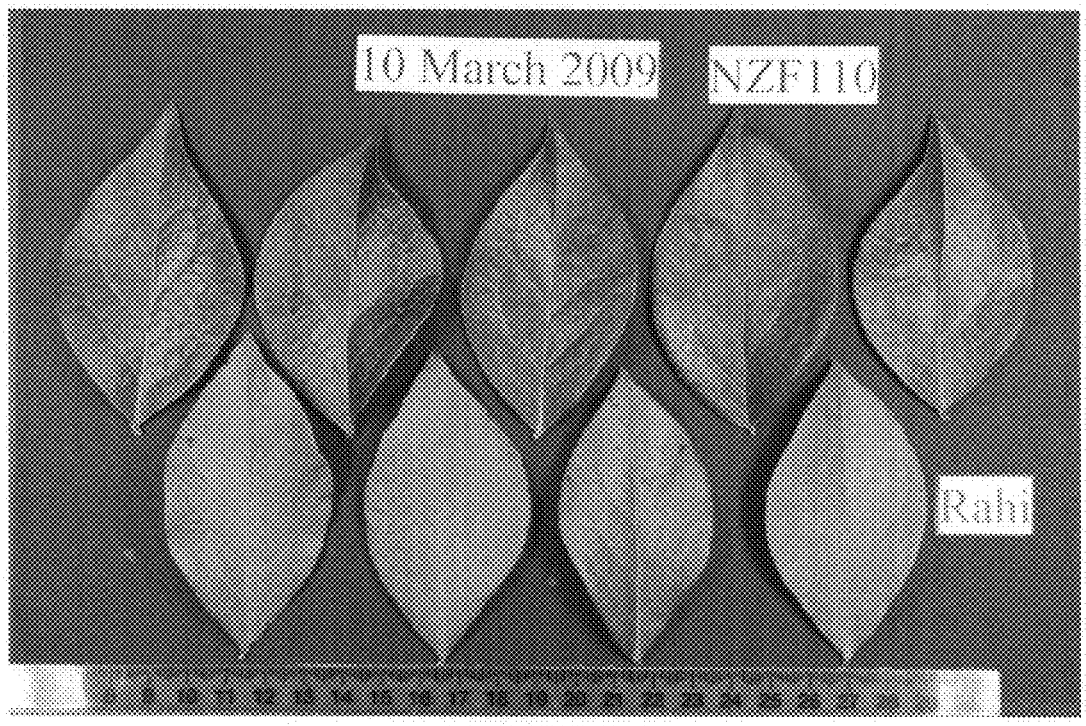
Figure 4:
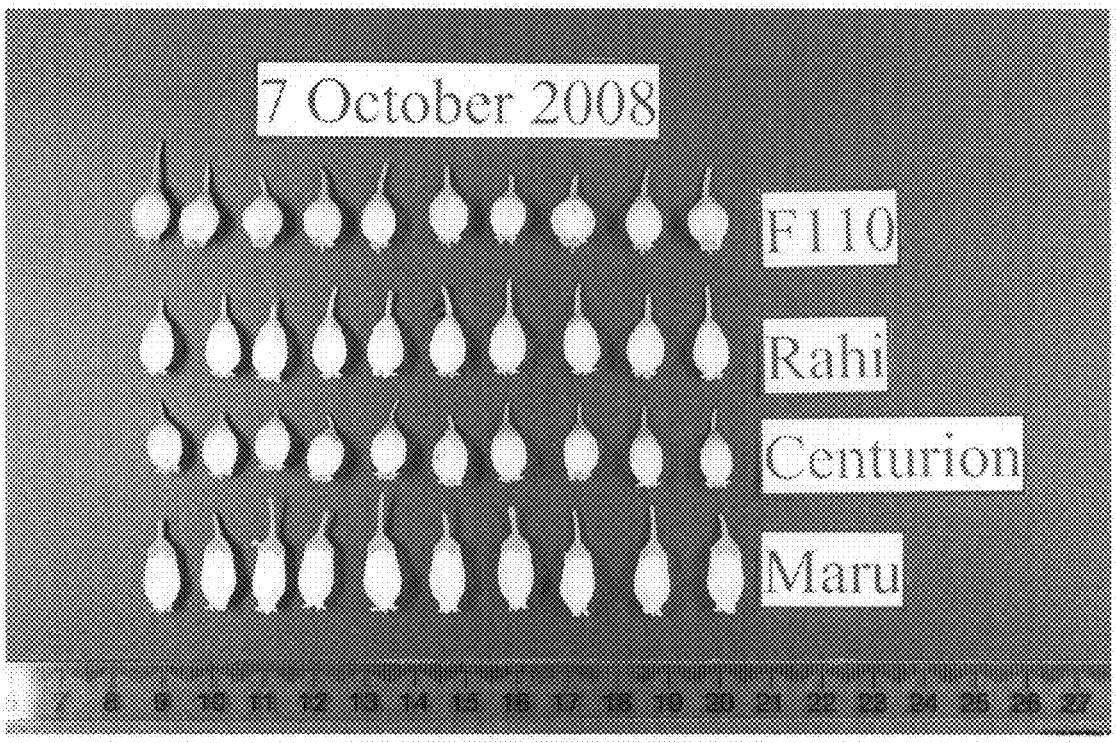
FIG. 4 shows the typical flowers collected from mature plants of 'Sky Blue' (labeled in the figure as 'F110') in October 2008 and compared to the flowers of commercial varieties 'Rahi', 'Centurion' and 'Maru'.
Figure 5:
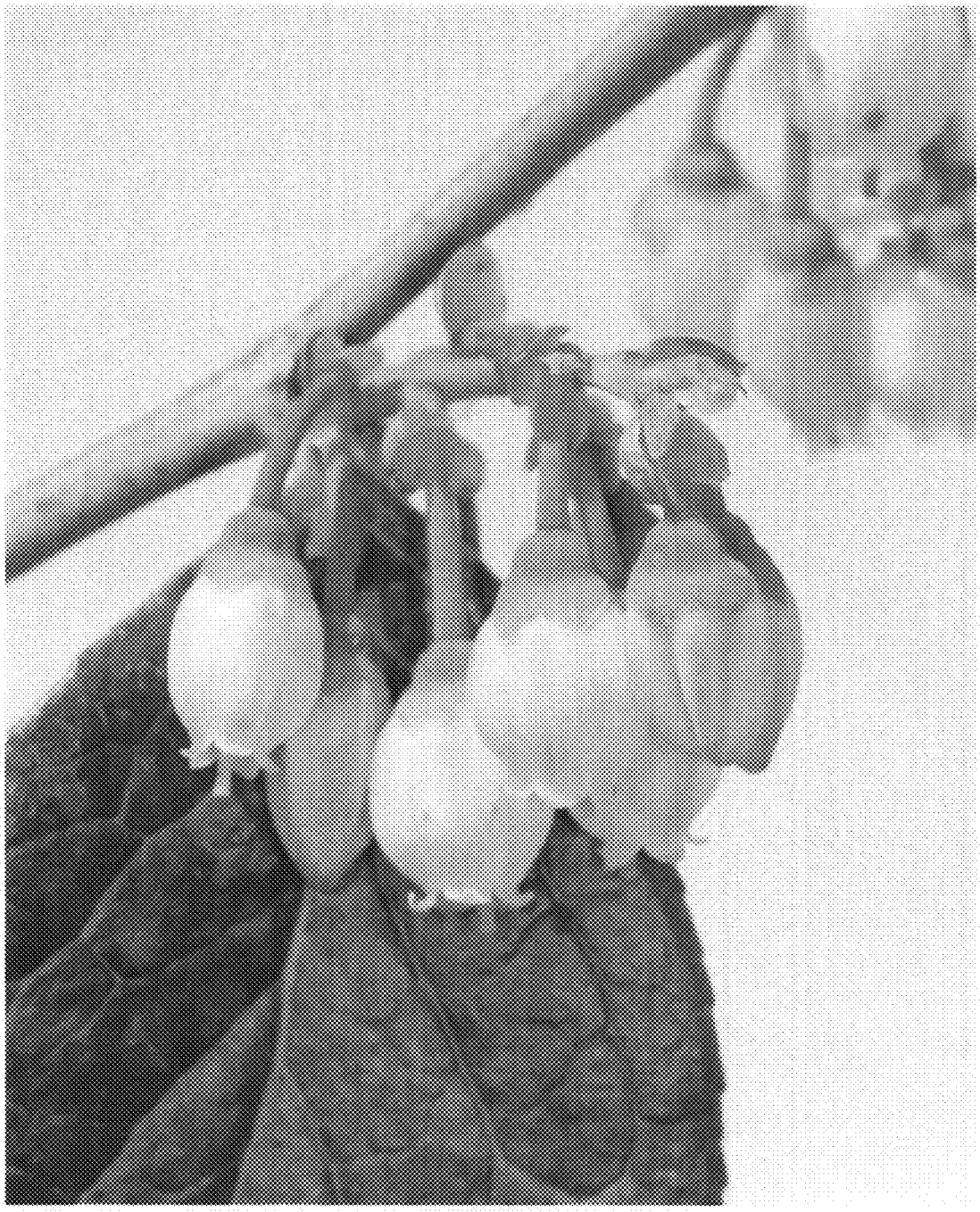
FIG. 5 shows a close up of the characteristic flowers coloration of 'Sky Blue'.
Figure 6:
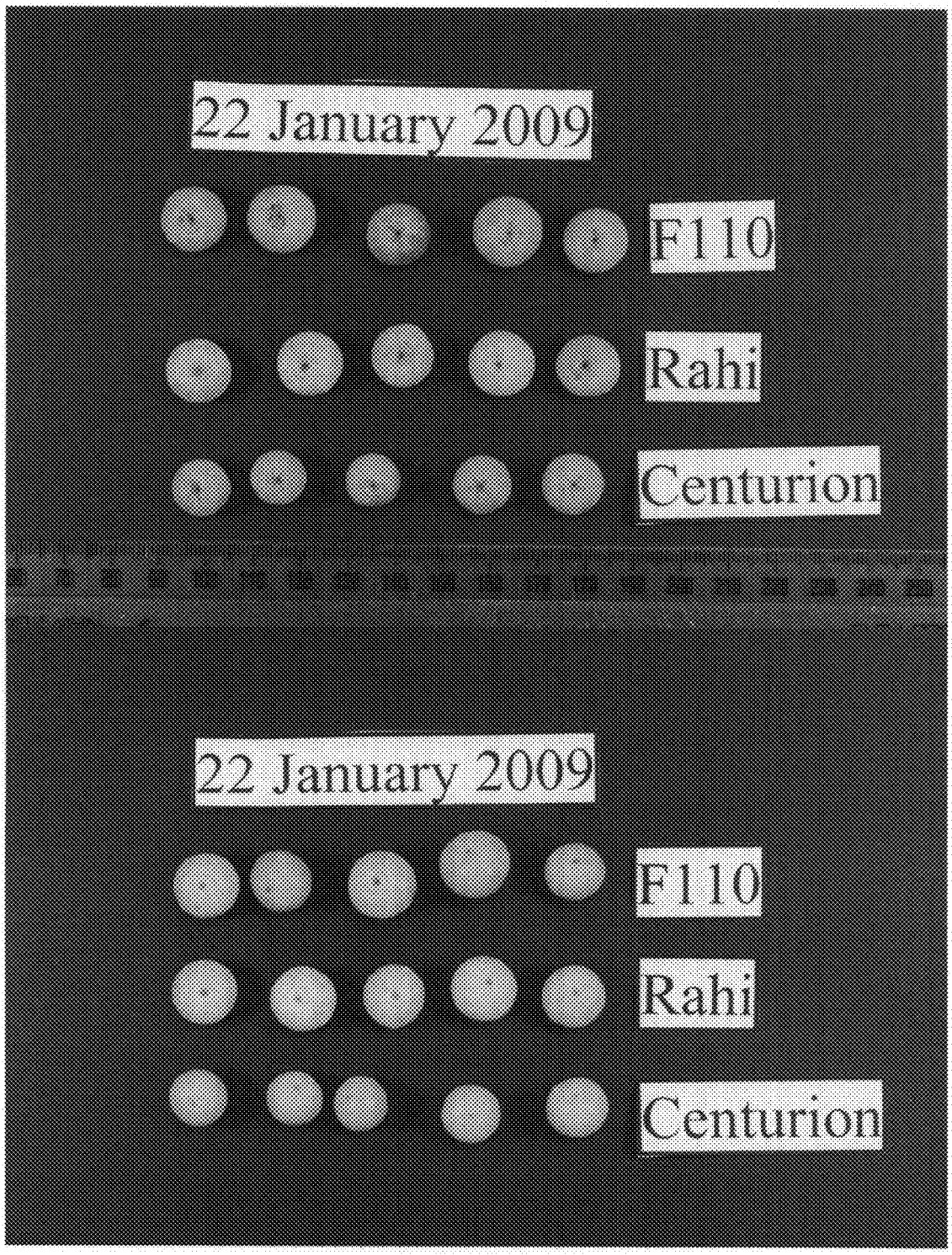
FIG. 6 shows the green fruit of 'Sky Blue' (labeled in the figure as 'F110') compared with the fruit of parental plants 'Centurion' and 'Rahi'.
Figure 7:
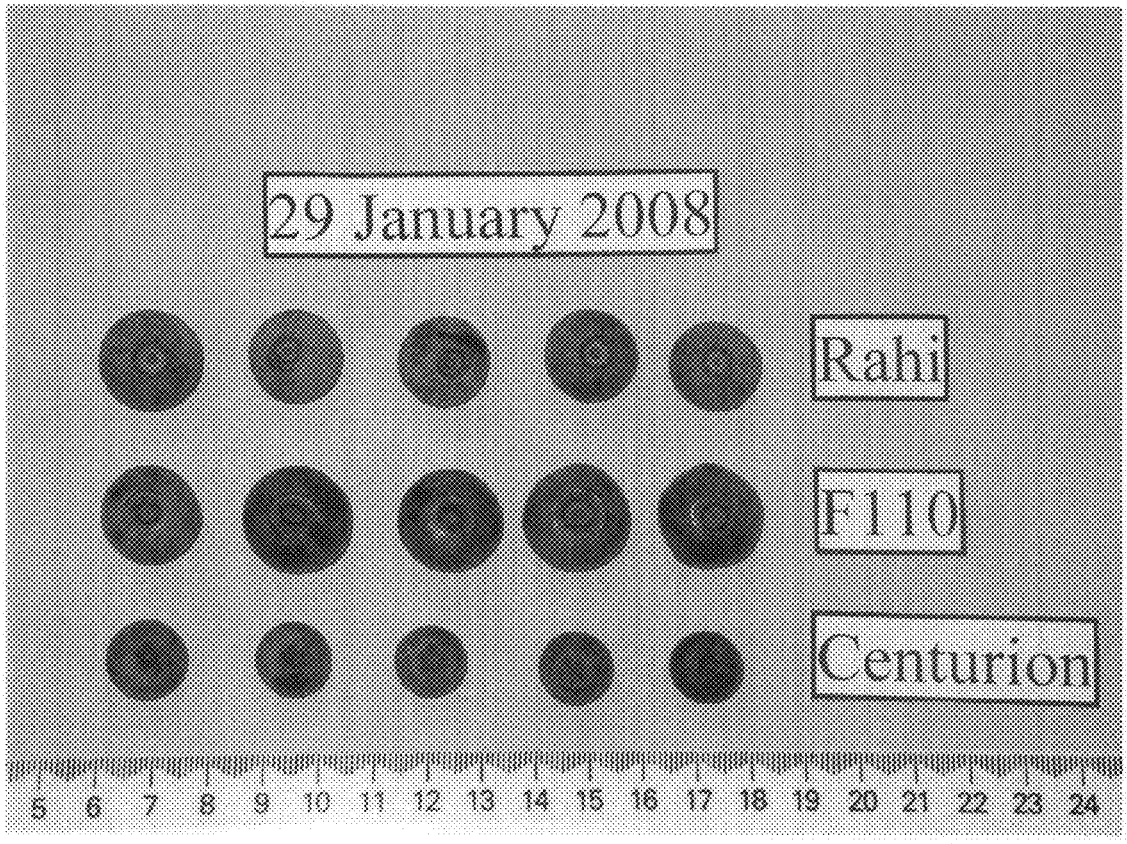
FIG. 7 shows typical large fruit of 'Sky Blue' (labeled in the figure as 'F110') compared with the fruit of parental plants 'Centurion' and 'Rahi'.

The observations, unless otherwise specified, were made in the 2008 and 2009 seasons on nine year old plants propagated and grown at Ruakura, Hamilton, New Zealand and additional information was collected from young plants (3-5 years old). All dimensions in millimeters, weights in grams (unless otherwise stated). Color terminology is in accordance with The Royal Horticultural Society Colour Charts 2001 edition.

Plant and foliage:

This hexaploid plant is generally upright with medium to good vigour. The mature leaf is lanceolate in shape and typically averages 74 mm in length and approximately 44 mm in width, similar to 'Rahi' (76 mm in length and 39 mm in width) and bigger than those of 'Centurion' (58 mm in length, 35 mm in width). Generally the leaf margin is serrate, medium to little glossiness on the upper surface, and no glaucescence on the upper surface. Typically the petiole length averages 3.2 mm. The color of the leaf is near Green 137B, differing to that of the parents 'Centurion' (near Green 137A) and 'Rahi' (near Green 137D). The leaf vein color is near Yellow-Green 148A.

The color of mature dormant wood is near Yellow-Green 148A on the top side of the cane and near Yellow-Green 148C on the underside of the same cane, differing from that of the parents 'Centurion' (near Red-Purple 60B on the top side of the cane and near yellow-green 146B on the underside of the same cane) and 'Rahi' (near Yellow-Green 146B and 146C on the top side of the cane and near Greyed-Red 178C of the same cane).

Inflorescence:

The average number of flower buds per shoot is 10, with an observed range of 5-18. The estimation of number of buds per shoot was made on the fruiting (terminal) sections of shoots; this section typically averaging 20 cm in length and the average total shoot length is 56 cm.

Flowers are generally clustered and the width of the typical flower averages 7.4 mm, larger than those of both 'Centurion' (averaging 6.5 mm) and 'Rari' (averaging 6.7 mm). The background color of the petals on fully open mature flowers is near White 155C and the anthocyanin coloration of the petals is near Red-Purple 68B and 68D, differing from those of the parents 'Centurion' and 'Rahi', both near White 155C with no anthocyanin coloration.

Fruit:

The fruit is large under New Zealand growing conditions, averaging approximately 2.4 g. Observations indicate fruit size is bigger than that of the parents 'Centurion' and 'Rahi' (averaging 1.4 g and 1.7 g respectively).

The fruit diameter of 'Sky Blue' averages approximately 17.3 mm (observed range 15-19 mm) under New Zealand growing conditions, bigger than that of the parents 'Centurion' and 'Rahi' (averaging 13.7 mm and 15.3 mm respectively). Unripe fruit is green, within the range near Yellow-Green 145B differing from the green fruit color of 'Centurion' and 'Rahi', both near to Yellow-Green 145A.

Ripe fruit of 'Sky Blue' has an attractive bloom. Fruit color is medium blue, with the bloom intact, near Blue 103C, differing from the variety 'Centurion' (near Blue 100C) and 'Rahi' (near Violet-Blue 98C). The skin color of the fruit of the variety 'Sky Blue' when bloom is completely removed is near Black 202A.

Observations indicate the pedicel scar of fruit of 'Sky Blue' is small, approximately 1.7 mm in diameter, similar to that of 'Rahi' (averaging 1.5 mm) and differing from those of 'Centurion' which were very small (1.1 mm). The scar is generally dry.

The fruit sweetness is high and the Brix level averaged 14.3%, (observed range 12.7-15%), intermediate between the fruit of the parental plants 'Rahi' and 'Centurion' (averaging 13.9 and 14.9 respectively).

The fruit acidity measured as titratable acidity (%) averaged 0.4 (observed range 0.3-0.5%), similar to 'Centurion' (0.5%). Fruit is generally firm, averaging 215 g/mm (observed range 200-235 g/mm) and similar to that of 'Rahi'. Yield is medium, averaging over 4 Kg per adult plant under New Zealand growing conditions.

Seed size is approximately 1.73 mm, with an average number of seeds per fruit of 43 (observed range approximately 20-66).

Events:

According to observations the time of vegetative bud burst was around the 10 September, about 10 days later than for the parents 'Centurion' and 'Rahi'. Time of beginning of flowering recorded in New Zealand was around one week after the vegetative bud break and reaching an estimated 50% of the flowering around the 8 October, similarly to 'Rahi'.

The fruit maturity period occurs in mid season, typically the fruit commences ripening around mid January to mid February at the Ruakura, Hamilton, New Zealand, In 2008 50% of blue fruit on the bush was estimated to occur about the 27 January, similar to 'Powderblue' and about one week later than 'Centurion' and 'Rahi'.

Disease and pests:

The plant showed symptoms in 2008 of the early stage of rust infection (*Pucciniastrum vaccinii*) with no subsequent sporulation and no defoliation.

The invention claimed is:

1. A new and distinct Rabbiteye blueberry variety substantially as described in the specification and illustrations.

* * * * *